United States Patent [19]

Williams

[11] Patent Number: 4,683,879
[45] Date of Patent: Aug. 4, 1987

[54] DUAL FUNCTION CONNECTOR FOR USE WITH ENDOTRACHEAL APPARATUS

[76] Inventor: R. Tudor Williams, 3423 Utah Crescent NW., Calgary, Alberta, Canada, T2N 4A9

[21] Appl. No.: 920,618

[22] Filed: Oct. 20, 1986

[51] Int. Cl.$^4$ ............................................. A61M 16/00
[52] U.S. Cl. .................................. 128/200.26; 128/4; 128/207.14; 128/6; 128/207.16
[58] Field of Search ...................... 128/4, 6, 10, 11, 22, 128/207.14, 207.15, 207.16, 207.17, 207.18, 200.26, 912

[56] References Cited

U.S. PATENT DOCUMENTS

| | | | |
|---|---|---|---|
| 4,041,936 | 8/1977 | Carden | 128/6 |
| 4,052,990 | 10/1977 | Dodgson | 128/207.14 |
| 4,291,691 | 9/1981 | Cabal et al. | 128/207.14 |
| 4,346,702 | 8/1982 | Kubota | 128/207.14 |
| 4,550,715 | 11/1985 | Santangelo et al. | 128/4 |
| 4,567,882 | 2/1986 | Heller | 128/11 |
| 4,580,556 | 4/1986 | Kondur | 128/6 |

*Primary Examiner*—Henry J. Recla
*Attorney, Agent, or Firm*—Nixon & Vanderhye

[57] ABSTRACT

A dual function connector for releasable attachment to an endopharyngeal tube, airway intubator or the like. The connector comprises a cylindrical tube having a large diameter proximal portion sized to fit within an airway intubator and a distal portion with a smaller diameter than the proximal portion. Flange means are provided on the proximal portion and extend substantially normal to the longitudinal axis of the connector; and an elongated slot in the connector extends from the distal end throughout the length of the distal portion and into the proximal portion.

3 Claims, 5 Drawing Figures

DUAL FUNCTION CONNECTOR FOR USE WITH ENDOTRACHEAL APPARATUS

FIELD OF THE INVENTION

This invention relates to connectors and in particular to a connector for use in resuscitation equipment or anaesthetic apparatus.

BACKGROUND OF THE INVENTION

The invention relates to apparatus used for intubation of the tracheal bronchial tree. There has for some time been a need for means that can be used with an airway intubator to provide for the passage of oxygen or anaesthetic gases into and out of the tracheal bronchial tree in combination with other apparatus such as a fiberoptic endoscope to facilitate oxygenation or ventilation.

U.S. Pat. No. 4,146,034 issued on Mar. 27, 1979 discloses an endotracheal tube connector, the end of which fits into an endotracheal tube, this connector having a specific configuration to facilitate its insertion into the tube and avoid damaging the latter during an assembly procedure. However, the subject matter of U.S. Pat. No. 4,146,034 falls short of providing the means for servicing the tracheal bronchial tree as described above.

Other U.S. patents in this general field are U.S. Pat. No. 4,346,702 which discloses means for passing sound waves downwardly into the lungs and also to facilitate insertion of the trachea without interfering with ventilation of the patient; U.S. Pat. No. 4,150,676 which discloses an endotracheal tube in which its radius of curvature can be changed; U.S. Pat. No. 2,912,982 which discloses an endotracheal adapter which has a hole for suction which can be cut off by opening and closing a threaded collar; and U.S. Pat. No. 4,054,135 which discloses the well-known Berman airway which is an oro-pharyngeal airway.

SUMMARY OF THE INVENTION

The dual function connector of the present invention can be used in combination with a specially shortened tube approximately one centimeter longer than an appropriate size airway intubator and which will provide an excellent airway for the passage of oxygen or anaesthetic gases in and out of the tracheal bronchial tree. Intermitent positive pressure ventilation can be obtained if an adhesive transparent dressing is applied to the face of the patient when an aperture has previously been made in the center of the dressing to fit over the proximal orifice of the airway intubator to be followed by the dual pupose connector of the present invention with the attached shortened tube. A fresh supply of gas is then connected to a universal attachment on the connector. This system then replaces the use of a face mask and airway system.

The apparatus of the invention can also be utilized in conjunction with a fiberoptic endoscope thereby providing means that will facilitate oxygenation and/or ventilation should either or both be desirable. In this mode of operation, the connector can receive the fiberoptic bronchoscope through a portion of its structure allowing the bronchoscope into the trachea and the previously ensleeved endotracheal tube can then be moved into the trachea on discarding the connector.

The function of the present invention includes the connection of anaesthetic apparatus or resuscitation equipment to a patient while using an airway intubator in conjunction with an adhesive transparent dressing. An intubator is placed in the patient's mouth and the patient's face is sealed off with an adhesive dressing apart from the above-mentioned orifice made over the proximal orifice of the intubator. A small oro-pharyngeal tube with a connector of the present invention attached, is passed through the adhesive transparent dressing to a short distance beyond the intubator.

The dimensions of the dual purpose connector of the present invention are such that there will be an airtight fit between the airway intubator and the anaesthesia or resuscitation equipment. Ventilation or spontaneous respiration can occur because the adhesive transparent dressing serves in lieu of the face mask and therefore there is no requirement to hold a mask on the patient's face, relieving a hand free for any other maneuvers that may be required.

Another function of the invention is to provide connection of anaesthesia or oxygen delivery apparatus during fiberoptic endoscopy intubation or for diagnostic bronchoscopy under general anaesthesia. An appropriate sized airway intubator is placed in the patient's mouth, an adhesive transparent dressing is placed over the patient's face and a dual purpose connector according to the invention, without any attachments, is then inserted part way into the intubator leaving a slot exposed that will allow for the entry of a fiberoptic endoscope. Manual ventilation or spontaneous respiration can occur with the system so arranged.

According to a broad aspect, the invention relates to a dual function connector for releasable attachment to a specially shortened oro-pharyngeal tube, airway intubator or the like, the connector comprising a cylindrical tube having a large diameter proximal portion sized to fit within an airway intubator and a distal portion with a smaller diameter than the proximal portion. Flange means are provided on the proximal portion and which extend substantially normal to the longitudinal axis of the connector and an elongated slot is provided in the connector, extending from the distal end throughout the length of the distal portion and into the proximal portion.

Preferably, the elongated slot terminates in the proximal portion in an area between the normally extending flanges and the smaller diameter distal portion.

The invention is illustrated by way of example in the accompanying drawings in which.

DETAILED DESCRIPTION OF THE PREFERRED EMBODIMENTS

Figure 2:
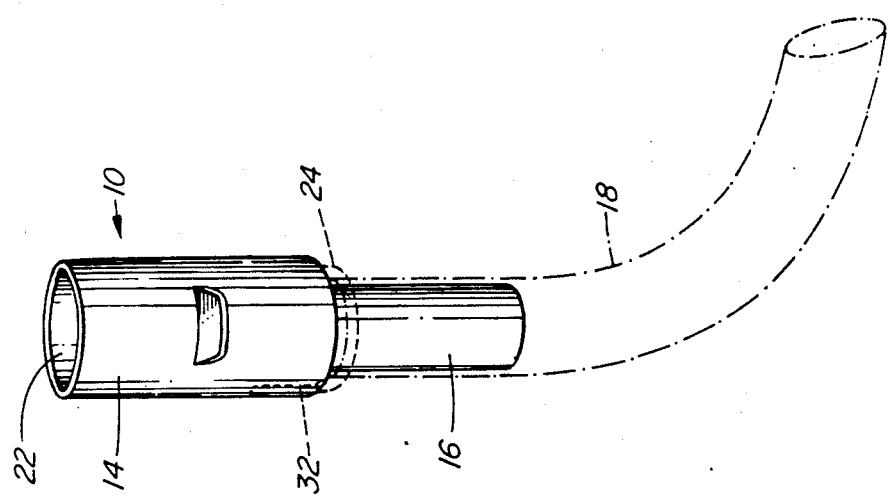
FIG. 2 is a perspective view similar to FIG. 1 but with the connector turned 90°.
Figure 1:
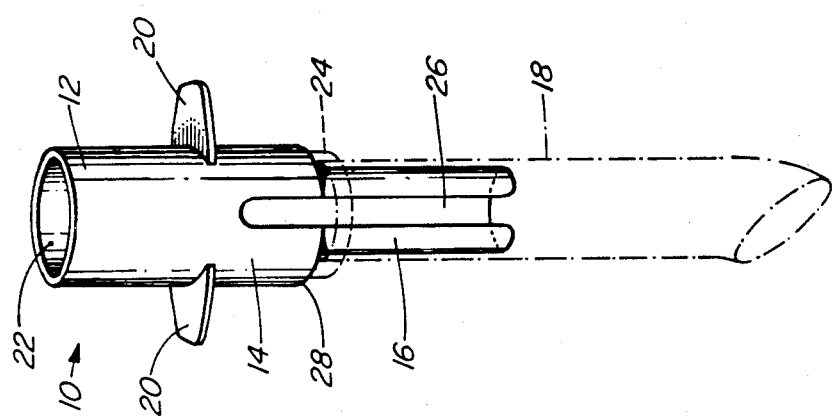
FIG. 1 is a perspective view of the connector of the present invention.

Referring to FIGS. 1 and 2, the dual function connector indicated generally at 10 comprises a cylindrical, tubular body 12 with a proximal portion 14 which is sized to fit within an airway intubator (FIGS. 3-5) and a distal portion 16 having a smaller diameter than the proximal portion and which may be used in combination with a specially shortened tube 18 shown in phantom line in FIGS. 1 and 2.

The proximal portion 14 has a pair of wings or flanges 20 which extend substantially normal to the longitudinal axis of the connector. These flanges facilitate connection of the proximal end 22 of the connector to an anaesthetic circuit of the like.

As shown in FIGS. 1 and 2, a short, depending collar 24, indicated in pecked line, can be included in the construction of the connector, the collar extending downwardly from the lower end of the proximal portion 14 and being concentric with and slightly larger in diameter than the distal portion 16 so that the connector will be inhibited from wobbling when it is withdrawn from the specially shortened tube 18 or from an airway intubator.

As clearly shown in FIG. 1, an elongated slot 26 is open at the lower terminal end of the distal portion 16 and extends upwardly throughout the length of the distal portion 16 and partially into the lower part of the proximal portion 14, terminating generally midway between the flanges 20 and the junction between the lower end of the proximal portion 14 and the upper end of the distal portion 16. Preferably, the upper terminal end of the slot 26 should be no closer than a half a centimeter from the flanges 20 on the proximal portion 14.

Figure 5:
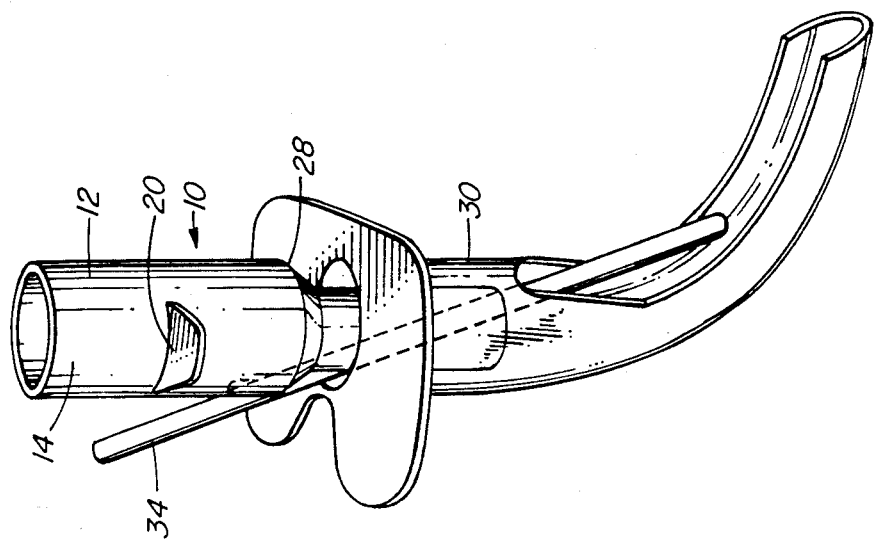
FIG. 5 is an elevation view showing the connector in combination with an airway intubator and a fiberoptic endoscope.
Figure 3:
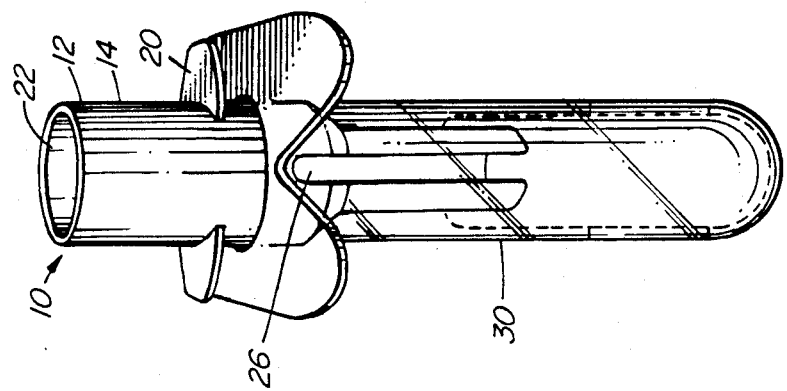
FIG. 3 is a perspective view showing the connector in combination with an airway intubator.
Figure 4:
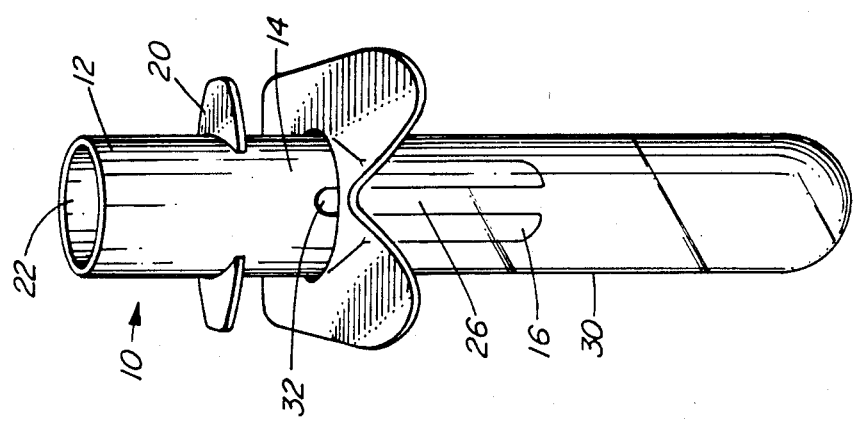
FIG. 4 is a view similar to FIG. 3 but showing the connector inserted further into the intubator.

The lower peripheral edge 28 of the proximal portion can be bevelled somewhat, as shown in FIGS. 3–5, so that the proximal portion 14 will more easily slide into the specially shortened tube 18 or an airway intubator 30, at the beginning of insertion.

Turning now to FIG. 3, the connector 10 is shown inserted into an airway intubator 30 so that the distal portion 16 and most of the proximal portion 14 are located within the intubator, to the point where the slot 26 is completely covered by the wall of the intubator 30. In FIG. 4, the connector 10 has been withdrawn slightly to expose the upper end 32 of the slot 26 outside of the confines of the intubator 30.

Referring to FIG. 5, with the slotted connector 10 placed into the proximal orifice of the intubator 30, oxygenation and ventilation of the patient can occur. If fiberoptic intubation is required, the connector is withdrawn slightly as in FIG. 4, exposing the upper end 32 of the slot 26 and the fiberoptic fiberscope 34 is then inserted through the exposed upper end 32 of the slot and into the trachea and the slotted connector 10 can then be discarded and the previously ensleeved endotracheal tube can be passed into the trachea. An airtight seal is utilized with the use of adhesive, transparent dressing on the patient's face.

During bronchoscopy oxygenation can occur by passing gases through the proximal orifice 22 and manual ventilation can occur if there is an airtight fit in place with the adhesive dressing as mentioned above.

While the invention has been described in connection with specific embodiments thereof and in specific uses, various modifications of the invention will occur to those skilled in the art without departing from the spirit and the scope of the invention as set forth in the appended claims.

The terms and expressions which have been employed in this specification are used as terms of description and not of limitation. There is no intention in the use of such terms and expressions to exclude any equivalents of the features shown and described or portions thereof, but it is recognized that various modifications are possible within the scope of the invention claimed.

I claim:

1. A dual function connector for releasable attachment to an endopharyngeal tube, airway intubator or the like, said connector comprising:

a cylindrical tube having a large diameter proximal portion sized to fit within an airway intubator and a distal portion with a smaller diameter than said proximal portion;

flange means on said proximal portion extending substantially normal to the longitudinal axis of said connector; and an elongated slot in said connector extending from said distal end throughout the length of said distal portion and into said proximal portion.

2. A connector according to claim 1, wherein the elongated slot terminates in said proximal portion in the area between said normally extending flanges and said smaller diameter distal portion.

3. A connector according to claim 1, including a peripheral collar projecting downwardly from said proximal portion to extend a short distance over said smaller diameter distal portion.

* * * * *